(12) United States Patent
Akutsu

(10) Patent No.: US 8,748,844 B2
(45) Date of Patent: Jun. 10, 2014

(54) SAMPLE ANALYZING APPARATUS AND SAMPLE ANALYZING METHOD

(75) Inventor: Haruko Akutsu, Yokosuka (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 13/605,580

(22) Filed: Sep. 6, 2012

(65) Prior Publication Data

US 2013/0248706 A1 Sep. 26, 2013

(30) Foreign Application Priority Data

Mar. 26, 2012 (JP) ................. 2012-069903

(51) Int. Cl.
*G01N 23/00* (2006.01)
*H01J 37/26* (2006.01)
*H01J 37/24* (2006.01)
*H01J 37/28* (2006.01)
*H01J 37/244* (2006.01)
*G01N 23/22* (2006.01)
*G01N 23/225* (2006.01)

(52) U.S. Cl.
CPC ............... *H01J 37/263* (2013.01); *H01J 37/26* (2013.01); *H01J 37/24* (2013.01); *H01J 37/28* (2013.01); *H01J 37/244* (2013.01); *G01N 23/22* (2013.01); *G01N 23/2251* (2013.01); *H01J 2237/221* (2013.01)
USPC ........... 250/399; 250/306; 250/307; 250/310; 250/311; 250/397

(58) Field of Classification Search
CPC ..... H01J 2237/221; H01J 37/26; H01J 37/28; H01J 37/24; H01J 37/244; H01J 37/263; G01N 23/22; G01N 23/2251
USPC ........... 250/306, 307, 309, 310, 311, 440.11, 250/442.11, 396 R, 397, 398, 399, 400
See application file for complete search history.

(56) References Cited

U.S. PATENT DOCUMENTS

| | | | | |
|---|---|---|---|---|
| 4,733,074 A * | 3/1988 | Kato et al. | ..................... | 250/307 |
| 4,897,545 A * | 1/1990 | Danilatos | ...................... | 250/310 |
| 5,608,218 A * | 3/1997 | Sato et al. | ..................... | 250/310 |
| 6,642,519 B2 * | 11/2003 | Ikeda | ........................... | 250/307 |
| 6,646,262 B1 * | 11/2003 | Todokoro et al. | ................ | 850/9 |
| 7,217,924 B1 * | 5/2007 | Mankos et al. | ............... | 250/310 |
| 8,288,724 B2 | 10/2012 | Kooijman et al. | | |
| 2004/0075054 A1 * | 4/2004 | Knippelmeyer | .............. | 250/310 |
| 2010/0258721 A1 | 10/2010 | Kooijman et al. | | |
| 2011/0139981 A1 * | 6/2011 | Fukaya et al. | ................ | 250/307 |
| 2011/0233399 A1 * | 9/2011 | Ichimura et al. | ............... | 250/307 |
| 2013/0094716 A1 * | 4/2013 | Carpio et al. | ................. | 382/109 |

FOREIGN PATENT DOCUMENTS

JP 2005-4995 1/2005

* cited by examiner

*Primary Examiner* — Michael Logie
(74) *Attorney, Agent, or Firm* — Finnegan, Henderson, Farabow, Garrett & Dunner, L.L.P.

(57) ABSTRACT

In accordance with an embodiment, a sample analyzing apparatus includes a charged beam generating unit, a detecting unit, and an analyzing unit. The charged beam generating unit is configured to generate a charged beam and apply the charged beam to a sample. The detecting unit is configured to detect charged particles and then output a signal, the charged particles being generated from the sample by the application of the charged beam in a manner depending on a three-dimensional structure and material characteristics of the sample. The analyzing unit is configured to process the signal to analyze the sample.

15 Claims, 15 Drawing Sheets

SAMPLE ANALYZING APPARATUS AND SAMPLE ANALYZING METHOD

CROSS REFERENCE TO RELATED APPLICATIONS

This application is based upon and claims the benefit of priority from the prior Japanese Patent Application No. 2012-069903, filed on Mar. 26, 2012, the entire contents of which are incorporated herein by reference.

FIELD

Embodiments described herein relate generally to a sample analyzing apparatus and a sample analyzing method.

BACKGROUND

In a semiconductor device manufacturing process, the following method has heretofore been used to analyze a sample. An electron beam is applied to the surface of the sample. Secondary electrons, reflected electrons, and others that are generated from the sample surface accordingly are detected, and signals are output. The obtained signals are then processed to analyze the material, structure, shape, and potential distribution of the sample. As an apparatus that enables such an analysis, for example, a scanning electron microscope (hereinafter briefly referred to as an "SEM") is used. The SEM generates a two-dimensional contrast image from the signals obtained by detecting the secondary electrons and reflected electrons from the sample.

In the conventional SEM, the enhancement of the resolution of the two-dimensional contrast image has been regarded as important. Accordingly, techniques have been developed to collect electrons generated from a sample as efficiently as possible to improve the S/N ratio.

This has caused the following problem. Electrons having different energy and different output vectors are collected, and secondary electrons that are spread in regard to energy come into one detector due to an interaction with the sample surface. As a result, information regarding the spread of the energy received from the sample surface is lost.

DETAILED DESCRIPTION

In accordance with an embodiment, a sample analyzing apparatus includes a charged beam generating unit, a detecting unit, and an analyzing unit. The charged beam generating unit is configured to generate a charged beam and apply the charged beam to a sample. The detecting unit is configured to detect charged particles and then output a signal, the charged particles being generated from the sample by the application of the charged beam in a manner depending on a three-dimensional structure and material characteristics of the sample. The analyzing unit is configured to process the signal to analyze the sample.

Embodiments will now be explained with reference to the accompanying drawings. Like components are provided with like reference signs throughout the drawings and repeated descriptions thereof are appropriately omitted.

(1) Embodiment 1

Figure 1:
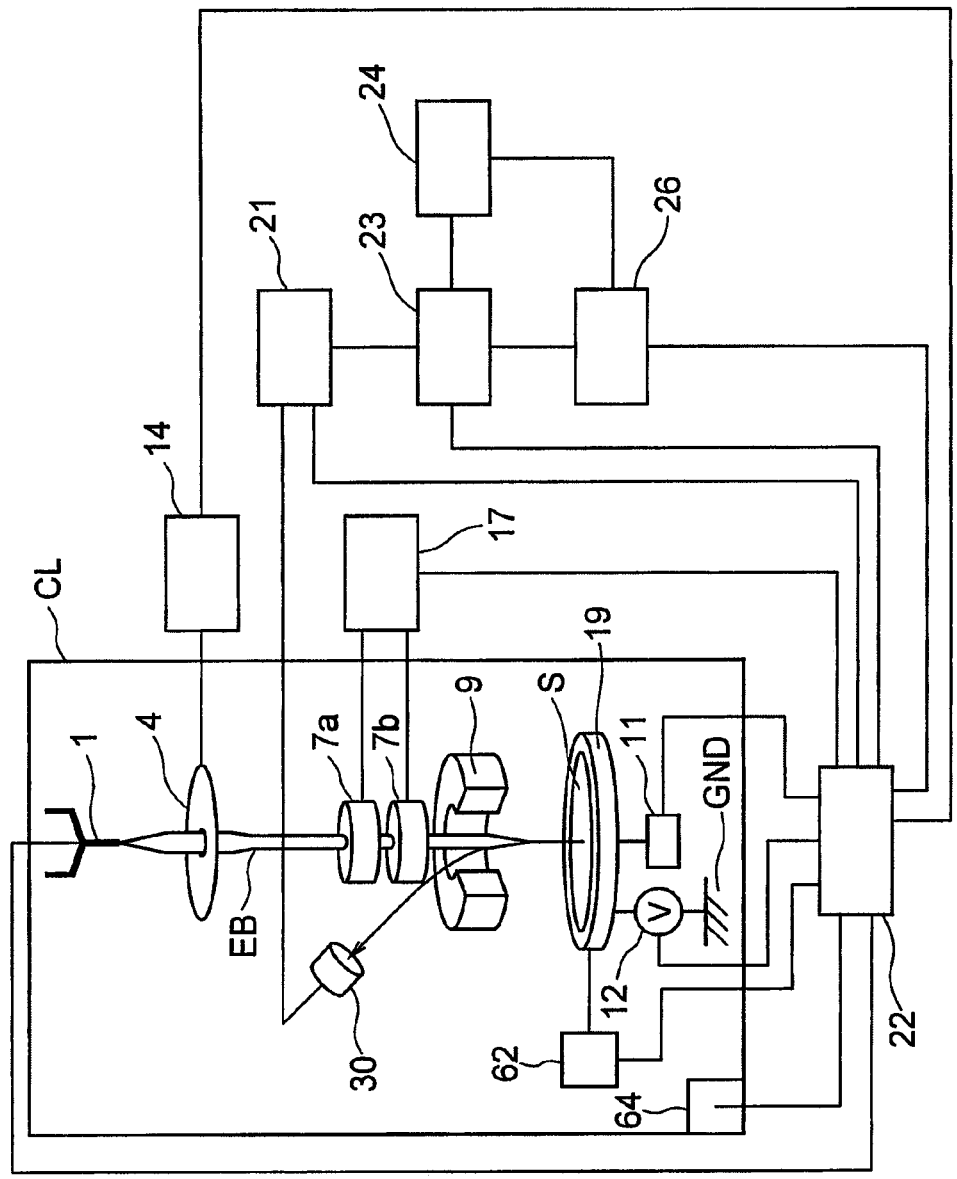
FIG. 1 is a block diagram showing a general structure of a sample analyzing apparatus according to Embodiment 1.

FIG. 1 is a block diagram showing a general structure of a sample analyzing apparatus according to Embodiment 1.

The sample analyzing apparatus according to the present embodiment includes a column CL, a condenser lens control unit 14, a deflection control unit 17, a signal processing unit 21, an image processing unit 23, a control computer 22, a sample analyzing unit 26, and a display unit 24. The column CL includes an electron gun 1, a condenser lens 4, beam scanning deflectors 7a and 7b, an objective lens 9, a stage 19, an actuator 11, a detector 30, a direct-current power supply 12, a stage temperature gauge 62, and a pressure gauge 64.

A sample S is mounted on the upper surface of the stage 19. The actuator 11 horizontally and vertically moves the sample S in response to a control signal from the control computer 22, and also inclines the sample S at a given angle θ (see FIG. 20) to a horizontal plane.

The direct-current power supply 12 applies a given voltage to the sample S via the stage 19 in accordance with the control signal sent from the control computer 22.

The electron gun 1 generates an electron beam EB, and applies the electron beam to the sample S. The electron gun 1 includes, but is not limited to, for example, a filament electrode, and has only to be able to generate the electron beam EB. In the present embodiment, the electron beam EB corresponds to, for example, a charged beam, and the electron gun 1 corresponds to, for example, a charged beam applying unit.

The condenser lens 4 generates a magnetic field or an electric field in accordance with a control signal sent from the condenser lens control unit 14, and converges the electron beam EB into a proper beam flux. The deflection control unit 17 generates a control signal in accordance with a command signal sent from the control computer 22, and sends the control signal to the condenser lens 4. In the present embodiment, the condenser lens 4 and the condenser lens control unit 14 correspond to, for example, a charged beam converging unit.

The objective lens 9 generates a magnetic field or an electric field, and again converges the electron beam EB so that the electron beam EB is applied just in focus to a given position in the surface or surface layer of the sample S. The beam scanning deflectors 7a and 7b are connected to the control computer 22 via the deflection control unit 17. The beam scanning deflectors 7a and 7b generate a magnetic field or an electric field to deflect the electron beam EB in accordance with a control signal which is generated by the deflection control unit 17 under the command signal from the control computer 22, thereby two-dimensionally scanning the sample S with the electron beam EB.

The detector 30 detects secondary electrons or reflected electrons generated from the sample S as a result of the application of the electron beam EB, and outputs and sends a signal to the signal processing unit 21. In the present embodiment, the secondary electrons or reflected electrons correspond to, for example, charged particles.

The signal processing unit 21 processes the signal sent from the detector 30 in accordance with a control signal sent from the control computer 22, and creates a contrast image (hereinafter referred to as a "potential contrast image") that reflects the potential distribution in the surface of the sample S.

In accordance with a control signal sent from the control computer 22, the image processing unit 23 performs computing processing, for example, to create a difference image for the potential contrast image sent from the signal processing unit 21. The generated potential contrast image and difference image are displayed by the display unit 24 which is, for example, a liquid crystal display.

The sample analyzing unit 26 receives the result of the computing processing from the image processing unit 23. The sample analyzing unit 26 analyzes the electric and physical states (physical properties) of the sample S, identifies the substance that constitutes the surface layer of the sample S, and outputs an analytic result of, for example, a particle size. The analytic result is displayed by the display unit 24. In the present embodiment, the image processing unit 23 and the sample analyzing unit 26 correspond to, for example, an analyzing unit.

The stage temperature gauge 62 measures the temperature of the stage 19, and provides the measurement result to the control computer 22. The pressure gauge 64 measures the pressure inside the column CL, and provides the measurement result to the control computer 22.

Figure 2:
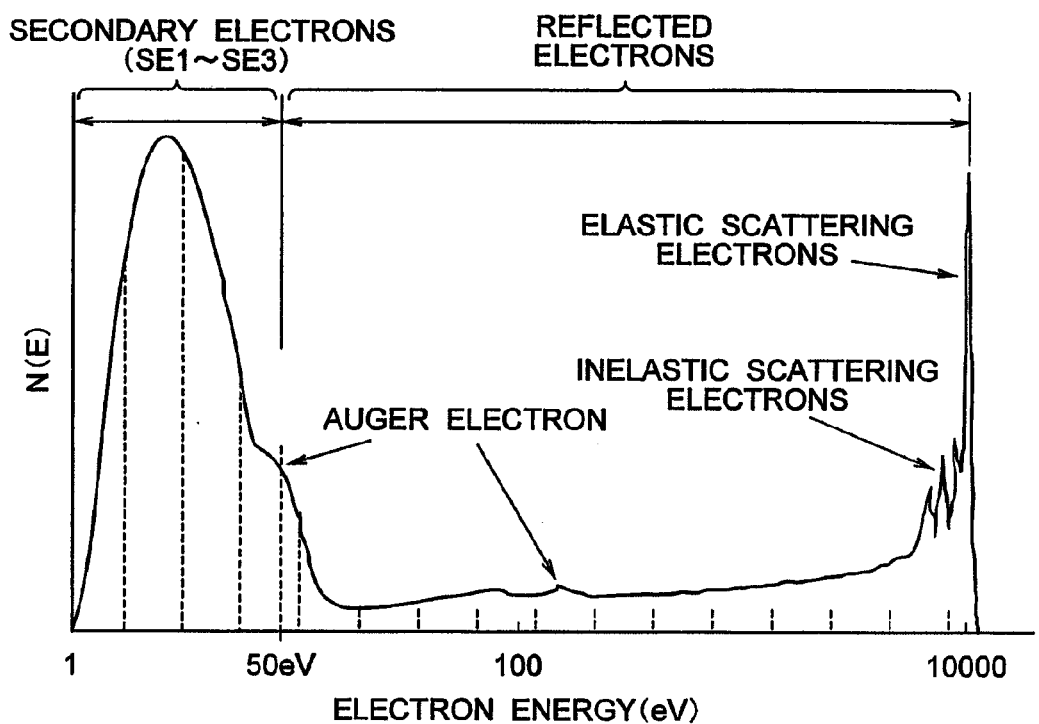
FIG. 2 is a graph showing an example of an energy distribution of electrons generated from a sample.

Here, electrons emitted from the sample S as a result of the application of the electron beam EB are described. FIG. 2 is a graph showing an example of an energy distribution of electrons generated from the sample S. In FIG. 2, electrons at 50 eV or less are referred to as secondary electrons, and electrons more than 50 eV fall under the category of reflected electrons.

Figure 3:
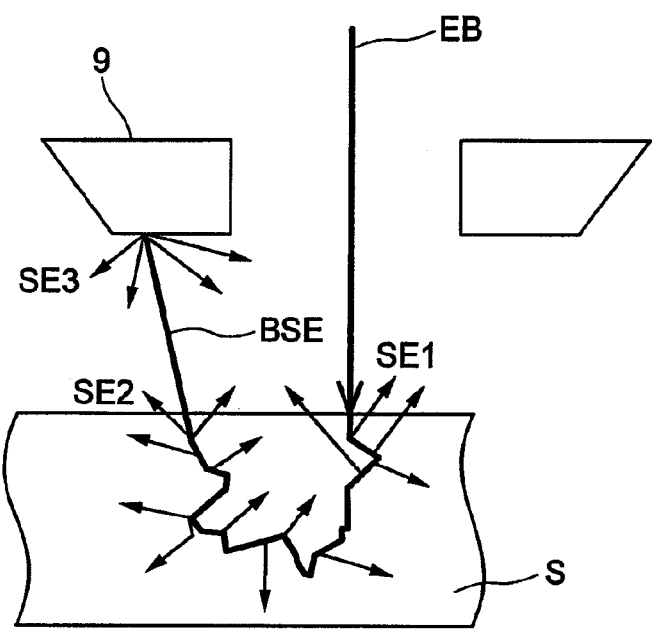
FIG. 3 is an explanatory view showing the generation forms of secondary electrons.

The secondary electrons are separated into SE1 to SE3 by their generation manners. FIG. 3 is an explanatory view showing the generation manners of the secondary electrons. Some of primary electrons of the electron beam EB applied to the surface of the sample S emit secondary electrons SE1 from the surface of the sample S due to an inelastic interaction. The secondary electrons SE1 are generated from the incidence point of the electron beam EB. Some of the rest of the primary electrons of the electron beam EB travel into the sample S, and are generated as back scattering electrons BSE due to more than one elastic interaction within the sample S. Some of the back scattering electrons BSE are emitted from a place remote from the focus of the electron beam EB as secondary electrons SE2 due to scattering within the sample. The rest of the back scattering electrons BSE are emitted from the sample S, collide with a member located in the vicinity within an optical system, in the example shown in FIG. 3, collide with the surface of the objective lens 9, and are reflected and transformed into secondary electrons SE3.

The secondary electrons SE1 to SE3 are rich in information regarding the material of the surface layer of the sample S as well as three-dimensional information regarding the micro unevenness of the surface of the sample S. In particular, the generation amount of the SE1 having energy of 10 eV or less varies with the work function of the material. Therefore, the detection of the difference of generation amount between the secondary electrons SE1 to SE3 enables a highly precise sample analysis. Among the secondary electrons SE1 to SE3, the secondary electrons SE1 are characterized in that a greater amount thereof are emitted in a direction right above the sample S as compared with the secondary electrons SE2 and SE3. Moreover, the secondary electrons SE1 have lower energy than the secondary electrons SE2 and SE3. Thus, the secondary electrons SE1 are characterized by being decreased in collection rate (the rate of a detection amount to an emission amount) if deflected by an electric field or a magnetic field before entering the detector 30. Accordingly, it is preferable to locate the detector 30 at a solid angle which is close to a direction perpendicular to the sample S in order to increase the collection rate of the secondary electrons SE1.

A sample analyzing method that uses the sample analyzing apparatus shown in FIG. 1 is described below.

Figure 4:
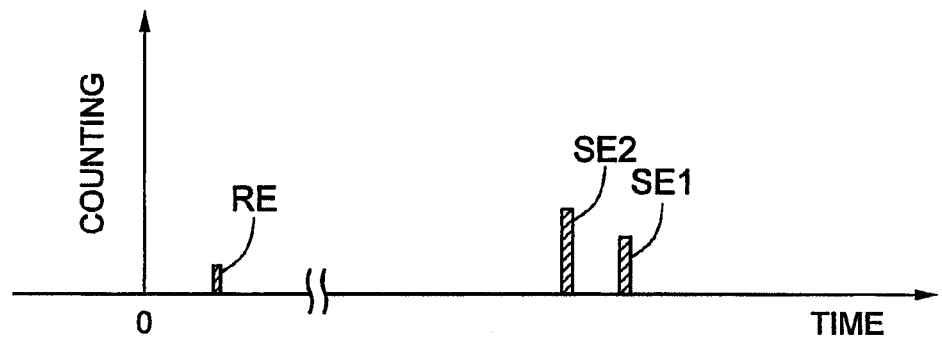
FIG. 4 is a graph showing an example of a time distribution of electrons generated from the sample.
Figure 5:
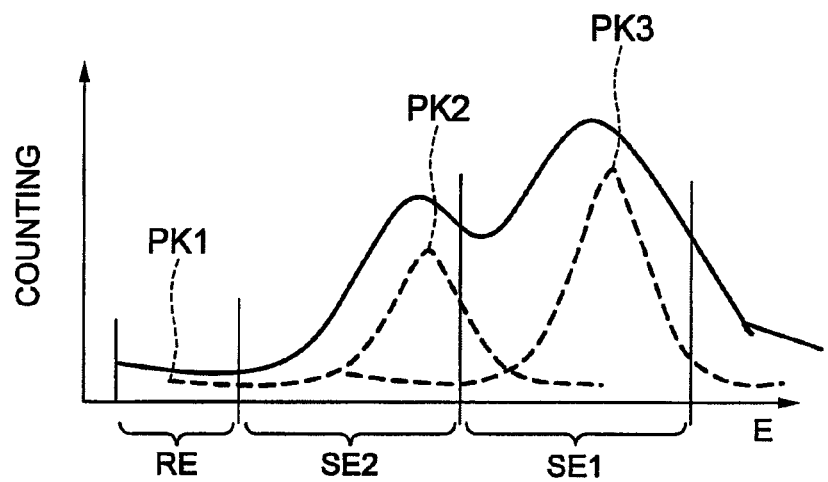
FIG. 5 is a graph showing an example of energy distributions of the electrons shown in FIG. 4.

Electrons generated from the sample S differ in the timing of being emitted from the sample S and entering the detector 30 in accordance with their energy levels. FIG. 4 is a graph showing an example of such a time distribution. Reflected electrons RE have energy close to the radiation energy of the electron beam EB, and are therefore the first to reach the detection surface of the detector 30. At the stage where the entrance of most of the reflected electrons RE has been finished, the secondary electrons SE2 and the secondary electrons SE1 reach the detector 30 in this order. Energy distributions of detection signals of the reflected electrons RE, the secondary electrons SE2, and the secondary electrons SE1 are shown in FIG. 5.

Thus, in the present embodiment, the timings of the peaks of the reflected electrons RE, the secondary electrons SE2, and the secondary electrons SE1 are preliminarily predicted. The image processing unit 23 subjects the signals obtained from the signal processing unit 21 to time resolution that uses, for example, Laplace transform, thereby separating the signals and generating their two-dimensional contrast images.

Figure 6:
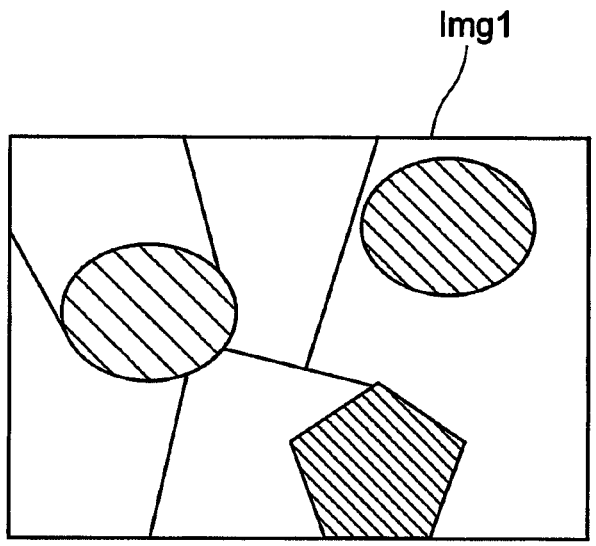
FIG. 6 is a diagram showing an example of a potential contrast image of reflected electrons.
Figure 7:
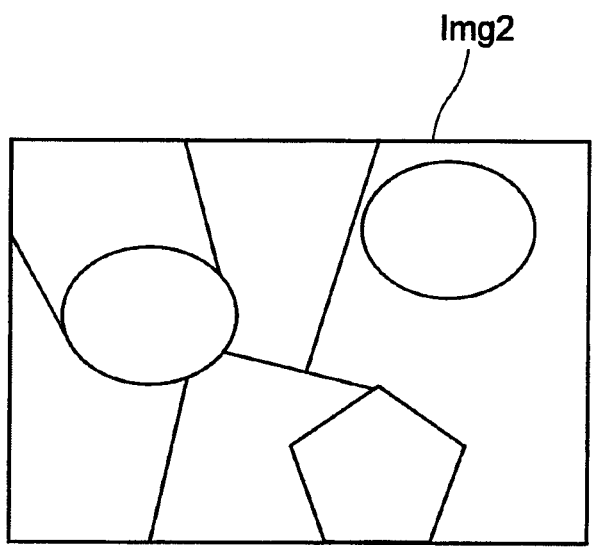
FIG. 7 is a diagram showing an example of a potential contrast image of SE2.
Figure 8:
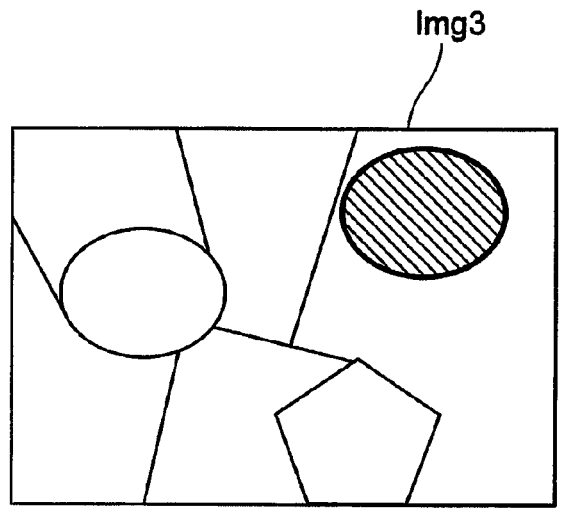
FIG. 8 is a diagram showing an example of a potential contrast image of SE1.

Specific examples of the two-dimensional contrast images thus obtained are shown in FIG. 6 to FIG. 8.

FIG. 6 is a diagram showing an example of a two-dimensional contrast image Img1 obtained for the reflected electrons RE. This image is generated from the detection signal extracted by the timing of a first peak PK1 in FIG. 5. Similarly, FIG. 7 and FIG. 8 show images which are generated from the detection signals of the SE2 and the SE1 extracted by the timings of second and third peaks PK2 and PK3 in FIG. 5.

The sample analyzing unit 26 processes these two-dimensional contrast images Img1 to Img3, and thereby analyzes the physical properties of the substance in the surface of the sample S. For example, the size of crystal grains in the surface substance of the sample S is calculated from the two-dimensional contrast image Img3 in FIG. 8.

In this way, according to the present embodiment, the detection signals are separated by the time resolution corresponding to the emission timing of the electrons. Therefore, a highly precise sample analysis can be conducted by a simple configuration.

(2) Embodiment 2

According to the present embodiment, the convergence angle of the electron beam EB is adjusted for signal separation. The sample analyzing apparatus shown in FIG. 1 can also be used for the present embodiment.

Figure 9:
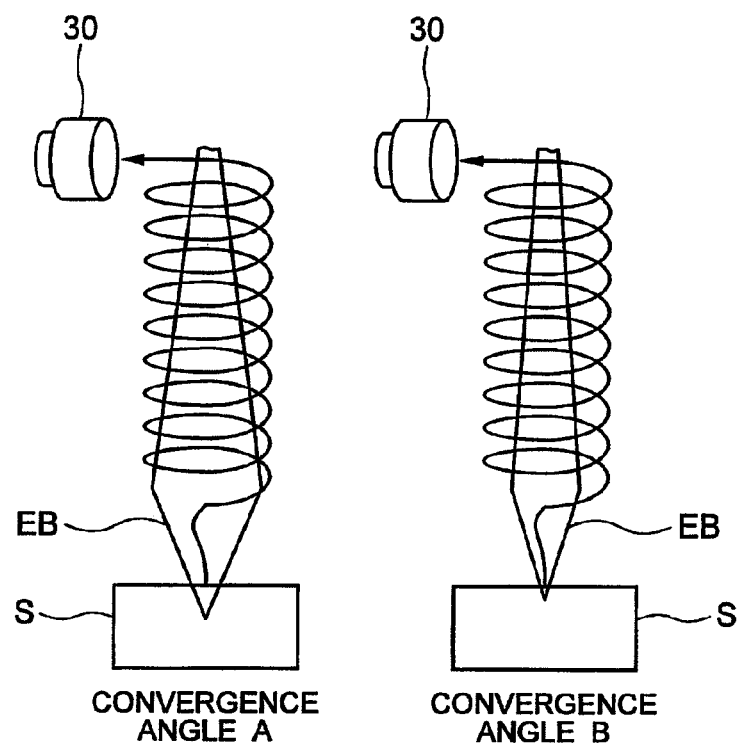
FIG. 9 is a diagram illustrating the changes of a beam flux and an image formation position attributed to the difference of convergence angles.

FIG. 9 is a diagram illustrating the changes of a beam flux and an image formation position attributed to the difference of convergence angles. As shown in FIG. 9, if the convergence angle of the electron beam EB radiating from the electron gun 1 is changed, the beam flux changes, and the position of image formation in the sample S changes. As a result, it is possible to not only obtain a two-dimensional contrast image in the surface of the sample S but also obtain a two-dimensional contrast image at a given depth within the sample S. A material distribution in the three-dimensional structure of the sample S can also be analyzed by the computation of these two-dimensional contrast images.

Figure 10:
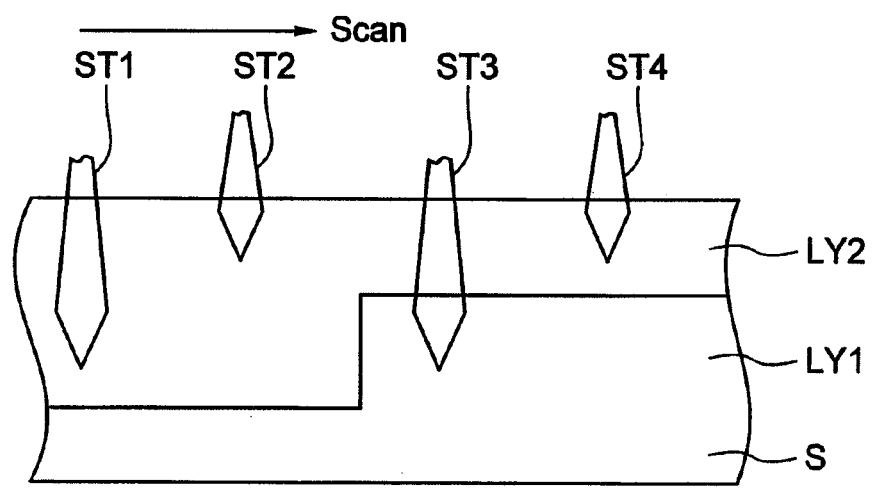
FIG. 10 is an explanatory view of a sample analyzing method according to Embodiment 2.

For example, as shown in FIG. 10, a first layer LY1 made of a material A is formed on a substrate in the surface layer structure of the sample S, and a second layer LY2 is formed on the first layer LY1. In this case, suppose that both the layers have the same thickness in design layout but the thickness has changed due to some problem in the process.

When this sample S is scanned with an electron beam from the left side of the drawing, there may be an unexpected change in a two-dimensional contrast image to be obtained if the convergence angle is changed at each shot. In this case, the problem in the manufacturing process can be discovered.

Figure 11:
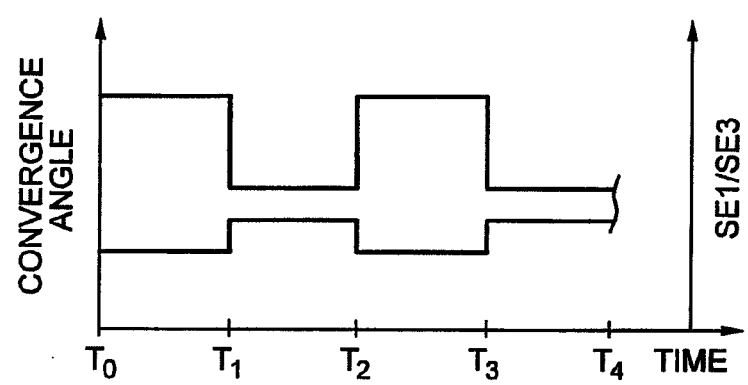
FIG. 11 is a timing chart showing an example of a control signal of a condenser lens according to Embodiment 2.

In the sample analyzing apparatus shown in FIG. 1, the condenser lens control unit 14 generates a control signal in accordance with a command signal sent from the control computer 22 so that, for example, the convergence angle changes A→B→A→B in shots ST1 to ST4 shown in FIG. 10. The condenser lens control unit 14 then sends the control signal to the condenser lens 4. The condenser lens 4 adjusts the beam flux of the electron beam EB to a convergence angle A at time intervals T0 to T1 and T2 to T3 in FIG. 11 and to a convergence angle B at time intervals T1 to T2 and T3 to T4.

In the example shown in FIG. 10, the electron beam EB is focused in the same layer LY2 in both the shots ST1 and ST2 at the time intervals T0 to T2. Thus, the same two-dimensional contrast image is obtained, and no difference image is obtained.

Figure 12:
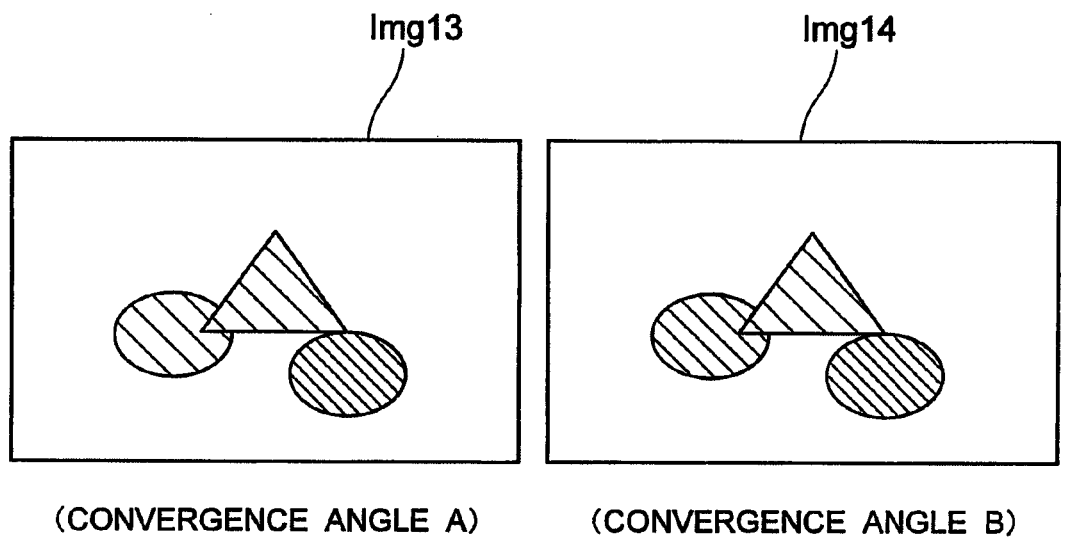
FIG. 12 is a diagram showing a specific example of potential contrast images obtained according to Embodiment 2.

On the other hand, at the time intervals T2 to T4, the thickness of the first layer LY1 is increased in a corresponding scan region, and the thickness of the second layer LY2 is decreased accordingly. Therefore, different two-dimensional contrast images are obtained. A specific example of such two-dimensional contrast images is shown in FIG. 12. In FIG. 12, a two-dimensional contrast image Img13 is an image obtained in the shot ST3 in FIG. 10, and a two-dimensional contrast image Img14 is an image obtained in the shot ST4 in FIG. 10.

Figure 13:
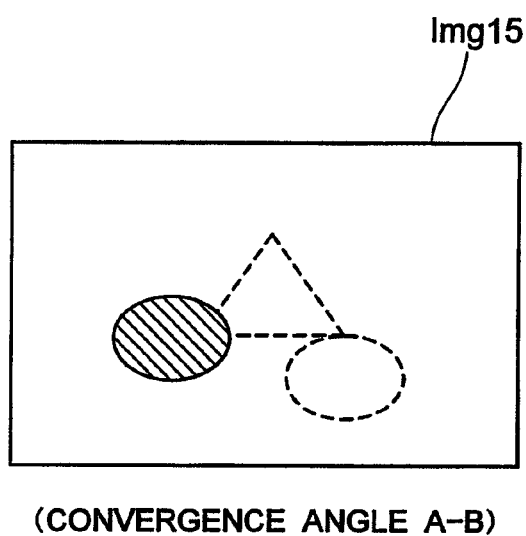
FIG. 13 is a diagram showing a difference image of the two potential contrast images shown in FIG. 12.

In the sample analyzing apparatus shown in FIG. 1, the image processing unit 23 then performs computing processing to create a difference image of these two-dimensional contrast images. Consequently, a difference image Img15 in which some of the particles remain as a result of the difference of materials between the layer LY1 and the layer LY2 is obtained as shown in FIG. 13. The sample analyzing unit 26 analyzes the difference image Img15 to find out that a three-dimensional structure different from the design layout is formed in the surface layer of the sample S.

According to the present embodiment, the sample surface is analyzed by the adjustment of the convergence angle of the electron beam EB and by the signal processing. Therefore, a highly precise sample analysis can be conducted by a simple configuration.

(3) Embodiment 3

Figure 14:
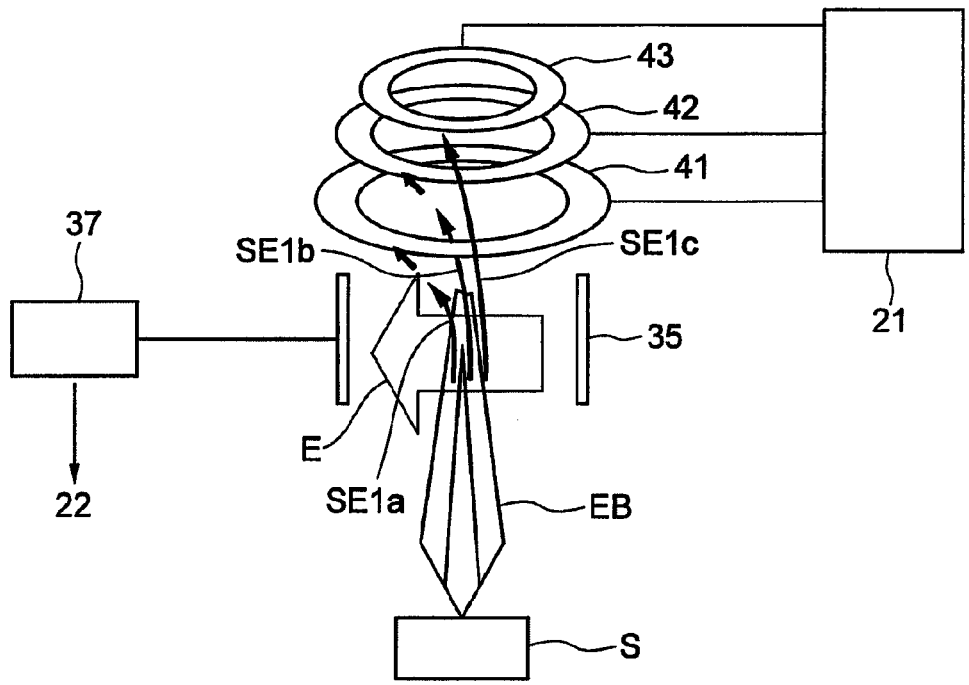
FIG. 14 is a diagram showing essential components of a sample analyzing apparatus according to Embodiment 3.

FIG. 14 is a diagram showing essential components of a sample analyzing apparatus according to Embodiment 3. In addition to the configuration in FIG. 1, the sample analyzing apparatus according to the present embodiment further includes ring-shaped detectors 41 to 43 placed apart from each other along the optical axis of the electron beam EB between the detector 30 and the sample S. The sample analyzing apparatus further includes an electron lens 35 disposed between the detector 41 and the sample S, and an electron lens control unit 37 which controls the electron lens 35 in response to a command signal provided from the control computer 22. The configuration of the sample analyzing apparatus according to the present embodiment is substantially the same in other respects as that of the sample analyzing apparatus shown in FIG. 1.

The detectors 41 to 43 are concentrically arranged around the optical axis, respectively. The diameter gradually increases from the detector 43 to the detector 41. Each of the detectors 41 to 43 is connected to the signal processing unit 21.

In the present embodiment, the electron lens control unit 37 generates a control signal in accordance with a command signal from the control computer 22. In response to this control signal, the electron lens 35 generates an electric field E. As a result, the radiation directions of the secondary electrons and the reflected electrons are deflected at angles corresponding to their energy, and a different detector can be used in detection for each energy band. In the example shown in FIG. 14, the reflected electrons RE and the secondary electrons SE2 enter the detector 30 (see FIG. 1), and SE1$c$, SE1$b$, and SE1$a$ of the secondary electrons SE1 respectively enter the detectors 43, 42, and 41 in descending order of energy.

The signal processing unit 21 individually processes signals sent from the detectors 41 to 43, and respectively generates two-dimensional contrast images.

It has heretofore been the case that the secondary electrons and the reflected electrons are all converged and detected to increase the S/N ratio of the two-dimensional contrast image. Therefore, pieces of information regarding the physical properties of the surface layer of the sample S are mixed, and the individual information cannot be extracted.

According to the present embodiment, signals are acquired by individually detecting the secondary electrons and the reflected electrons in accordance with the energy levels of electrons emitted from the sample S. Thus, physical property information corresponding to the energy of each kind of electron can be acquired. In the present embodiment, the electron lens 35 and the electron lens control unit 37 correspond to, for example, a trajectory control unit.

(4) Embodiment 4

Figure 15:
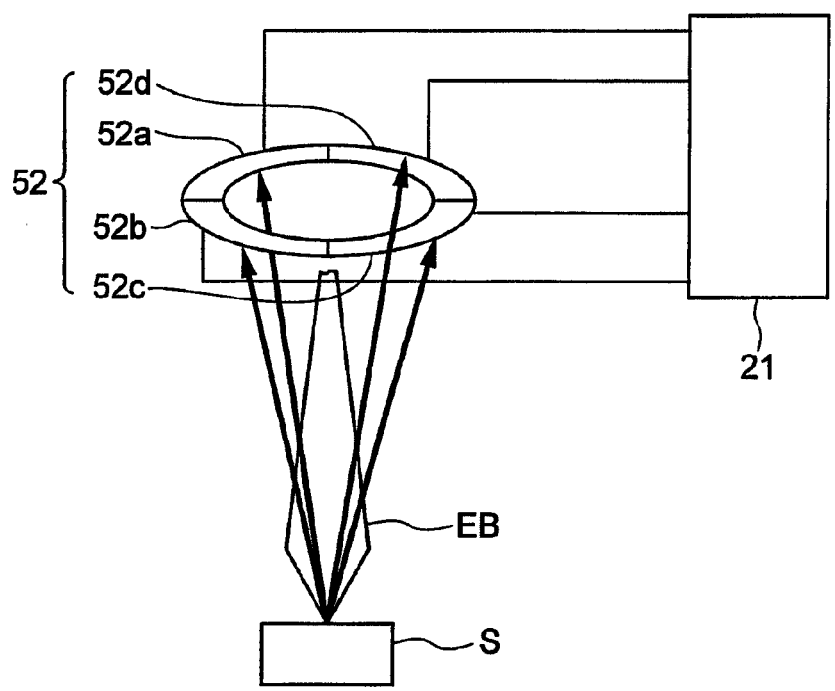
FIG. 15 is a diagram showing essential components of a sample analyzing apparatus according to Embodiment 4.
Figure 17:
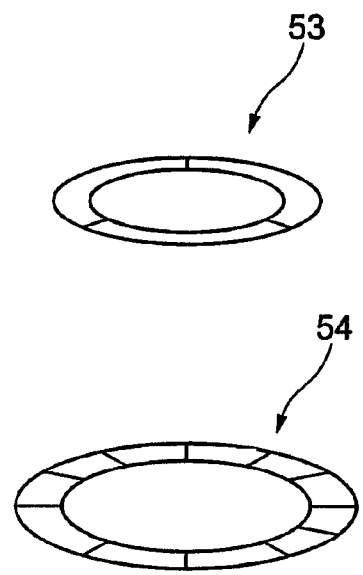
FIG. 17 is a diagram showing another example of a detector provided in the sample analyzing apparatus shown in FIG. 15.

FIG. 15 is a diagram showing essential components of a sample analyzing apparatus according to Embodiment 4. The sample analyzing apparatus according to the present embodiment includes, instead of the detector 30 in FIG. 1, a ring-shaped detector 52 disposed around the optical axis of the electron beam EB in a plane that intersects at right angles with this optical axis. The detector 52 is divided into four regions 52a to 52d, and detection signals of the respective regions are sent to the signal processing unit 21 and individually processed. The detector 52 is divided into the regions so as to correspond to the symmetry of crystal in the surface or surface layer of the sample S. The detector 52 is not exclusively divided into four regions, and may be divided into other numbers of regions in accordance with the crystal to be analyzed, for example, may be divided into three regions as in a detector 53 shown in FIG. 17. However, if crystal point groups are taken into consideration, a common multiple of three and four is preferable. A detector 54 shown in FIG. 17 is an example that is divided into twelve which is a common multiple of three and four.

The secondary electrons and the reflected electrons generated from the sample S are emitted in different directions depending on the orientation of the crystal to be analyzed. Thus, the signals from the divided regions of the detector are processed to respectively create two-dimensional contrast images. These two-dimensional contrast images are compared and subjected to addition and subtraction. Consequently, the crystal orientation can be determined, and the substance in the surface layer of the sample S can be identified.

Figure 16:
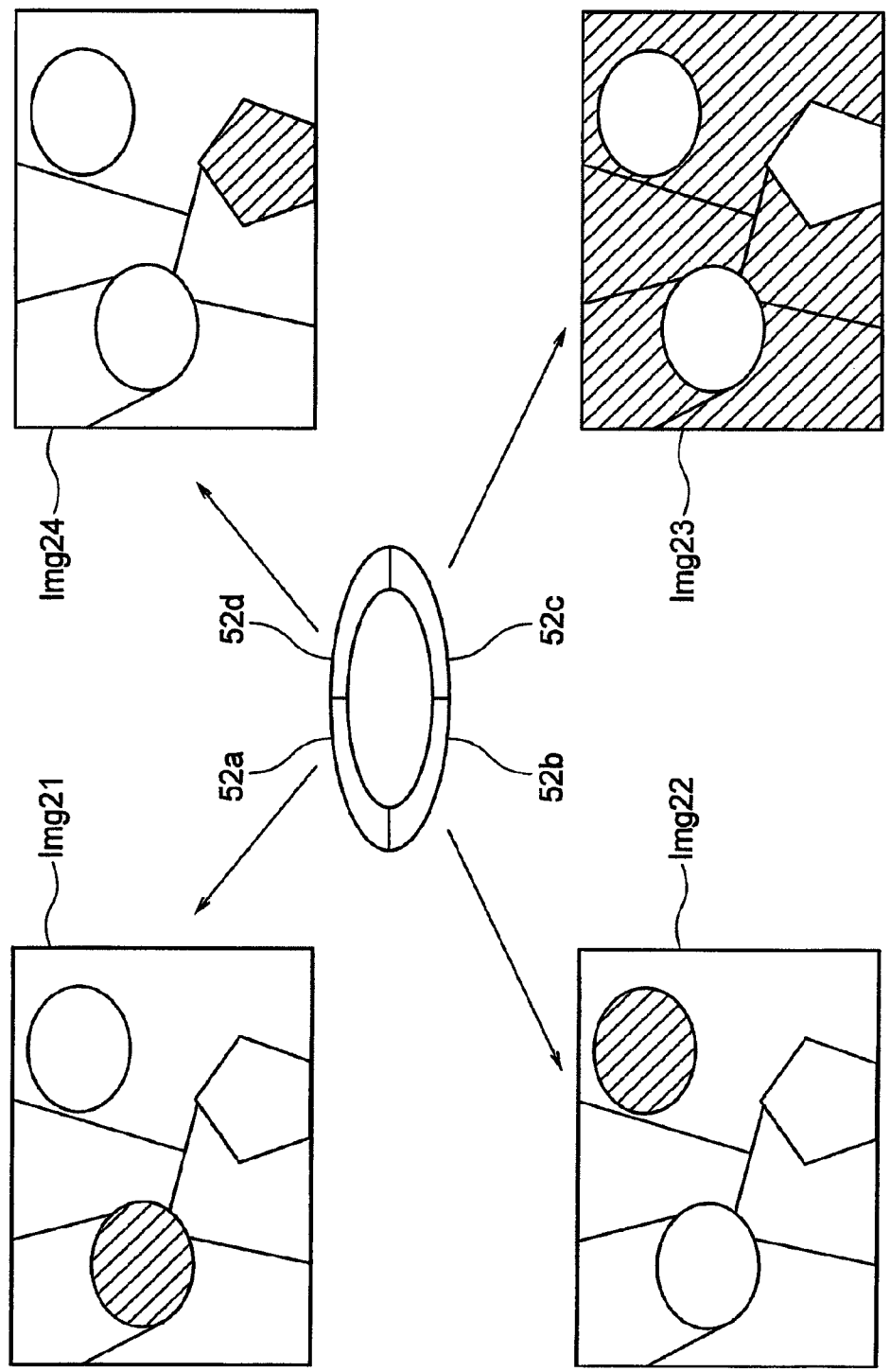
FIG. 16 is an explanatory view of a method of identifying a substance in the surface layer of a sample by the sample analyzing apparatus shown in FIG. 15.

FIG. 16 is a schematic view illustrating such an identifying method. The electron beam EB is applied to the sample S, and the secondary electrons and the reflected electrons generated from the sample S are detected by the regions 52a to 52d of the detector 52. The image processing unit 23 processes the detection signals from the regions 52a to 52d to generate two-dimensional contrast images Img21 to Img24. The sample analyzing unit 26 performs computing processing for the two-dimensional contrast images Img21 to Img24 to analyze the crystal orientation of the part to which the electron beam EB has been applied. The sample analyzing unit 26 then refers to a prepared table, and thereby identifies the substance in the surface layer of the sample S.

According to the present embodiment, the secondary electrons and the reflected electrons are detected in accordance with the orientation of the crystal to be analyzed. Therefore, a target substance can be highly precisely identified by a simple configuration.

(5) Embodiment 5

Figure 18:
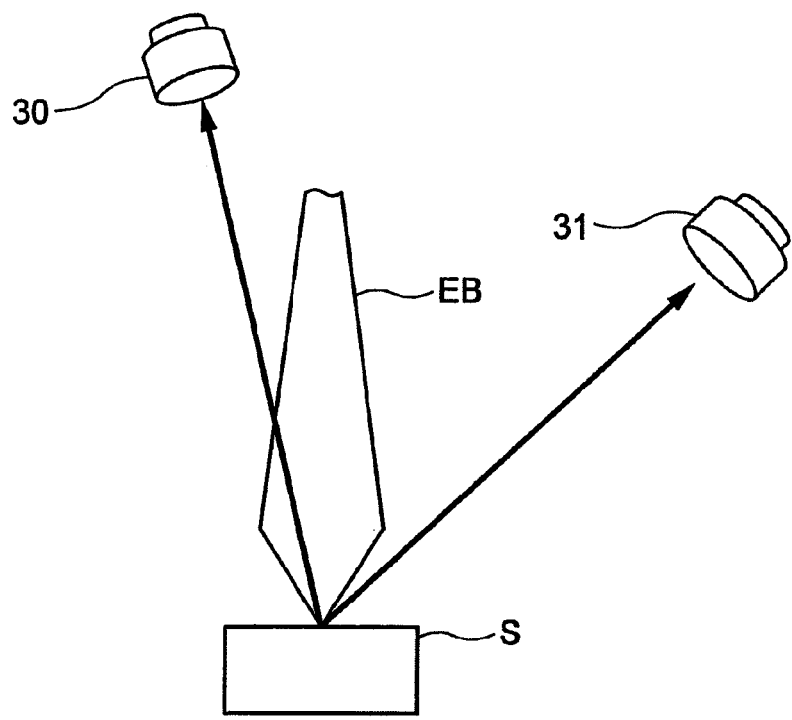
FIG. 18 is a diagram showing essential components of a sample analyzing apparatus according to Embodiment 5.

FIG. 18 is a diagram showing essential components of a sample analyzing apparatus according to Embodiment 5. In addition to the configuration in FIG. 1, the sample analyzing apparatus according to the present embodiment further includes a detector 31 disposed at a solid angle different from the solid angle of the detector 30. The configuration of the sample analyzing apparatus according to the present embodiment is substantially the same in other respects as that of the sample analyzing apparatus shown in FIG. 1. Although the two detectors 30 and 31 are provided for the simplification of explanation in the example shown in FIG. 18, the detectors are not limited in number, and three or more detectors may be provided depending on the properties of an analytic object.

For the solid angles of the detectors, values at which the secondary electrons and the reflected electrons from the crystal orientation are easily detected are selected in accordance with a target analytic object. The reasons are as follows. If the solid angle of the detector is adapted to the crystal orientation, the two-dimensional contrast image obtained by the detection signal is bright (has high luminance). If, on the other hand, the solid angle is not adapted to the crystal orientation, the two-dimensional contrast image is dark (has low luminance).

Figure 19:
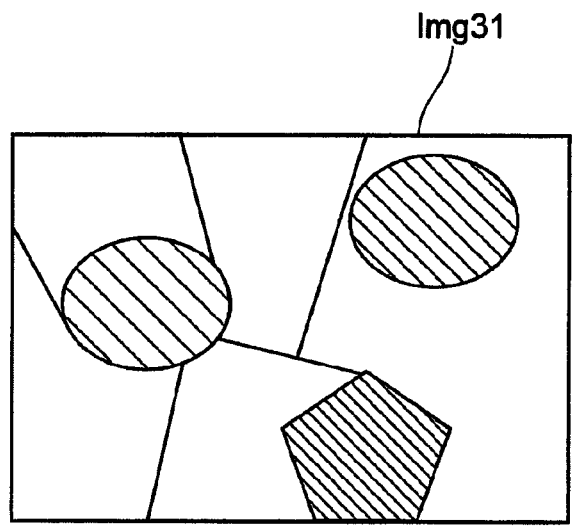
FIG. 19 is a diagram showing an example of a two-dimensional contrast image obtained by the sample analyzing apparatus shown in FIG. 18.

In a sample analysis, the electron beam EB is applied to the sample S from the electron gun 1, and the secondary electrons and the reflected electrons generated from the sample S are detected by the detectors 30 and 31. Signals from the detectors 30 and 31 are sent to the image processing unit 23. In the present embodiment, the image processing unit 23 simultaneously processes these signals and generates a two-dimensional contrast image. A two-dimensional contrast image Img31 shown in FIG. 19 is an example of a two-dimensional contrast image thus obtained.

Figure 20:
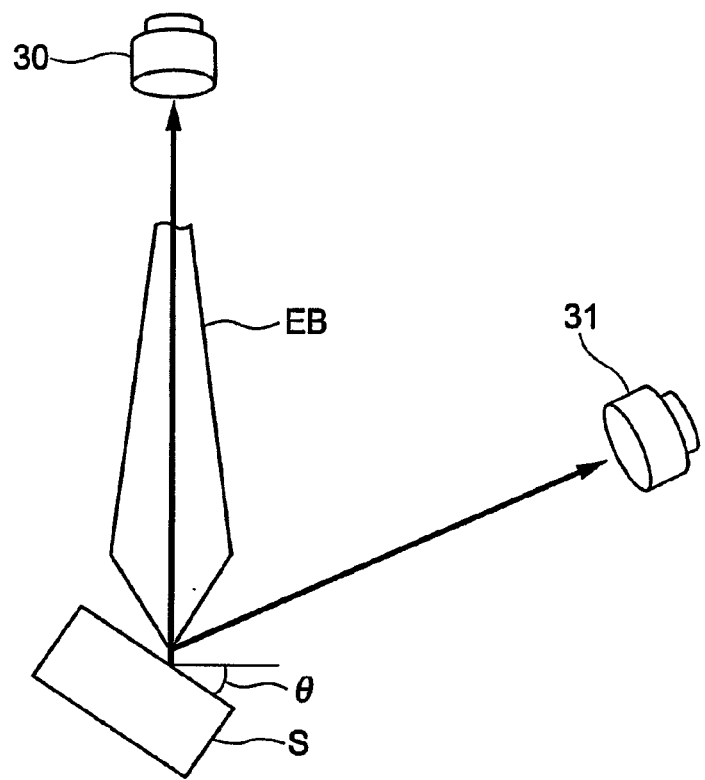
FIG. 20 is a diagram showing how a sample is inclined and observed by the sample analyzing apparatus shown in FIG. 18.
Figure 21:
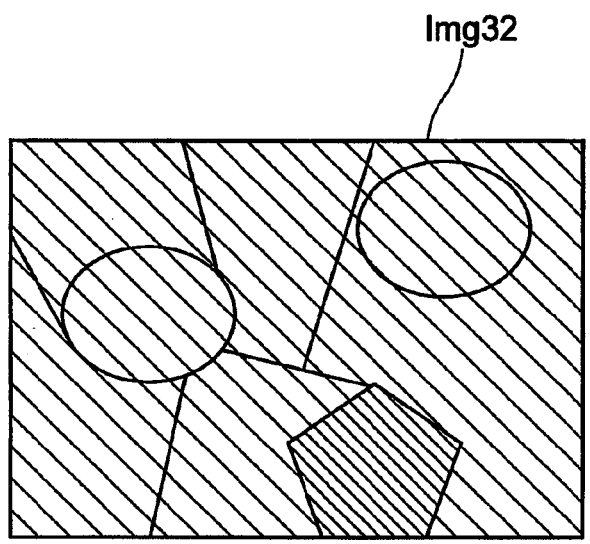
FIG. 21 is a diagram showing an example of a two-dimensional contrast image obtained when the sample is inclined by the sample analyzing apparatus shown in FIG. 18.

The actuator 11 (see FIG. 1) is then actuated by a control signal of the control computer 22, and the sample S is inclined at a given angle θ as shown in FIG. 20. In this condition, the electron beam EB is applied, and the secondary electrons and the reflected electrons generated from the sample S are again detected by the detectors 30 and 31, and then a two-dimensional contrast image is generated by the image processing unit 23. A two-dimensional contrast image Img32 shown in FIG. 21 is an example of a two-dimensional contrast image thus obtained.

Figure 22:
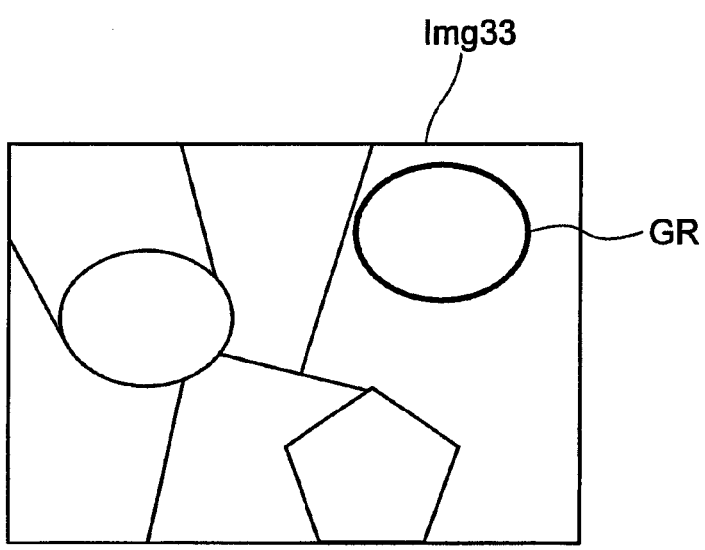
FIG. 22 is a diagram showing a difference image of the two-dimensional contrast image shown in FIG. 19 and the two-dimensional contrast image shown in FIG. 21.

The sample analyzing unit 26 receives, from the signal processing unit 21, data on the two-dimensional contrast image thus obtained, and performs computing processing to evaluate the crystallinity of the substance in the surface layer of the sample S. FIG. 22 shows a difference image Img33 of the two-dimensional contrast image Img31 shown in FIG. 19 and the two-dimensional contrast image Img32 shown in FIG. 21, which is obtained by the computing processing in the sample analyzing unit 26. In the example shown in FIG. 22, the border of a crystal GR sharply stands out, and its size can be calculated by image processing.

(6) Embodiment 6

In the present embodiment, a bias voltage is applied to the sample S to compensate for the electrification of the sample. The sample analyzing apparatus shown in FIG. 1 can be used.

If the sample S is continuously scanned with the electron beam EB, the sample S may be electrified by the continuous application of the electron beam EB. In this case, the contrast of the two-dimensional contrast image to be obtained is lower. The influence of the electrification also depends on the structure of the sample to be analyzed. For example, when one layer of a PN junction includes an isolated pattern, even slight electrification may prevent observation.

Thus, in the present embodiment, a voltage is applied to the sample S during the interval of scans with the electron beam EB to supply a charge (hole), and the electrification is thereby eased.

Figure 23:
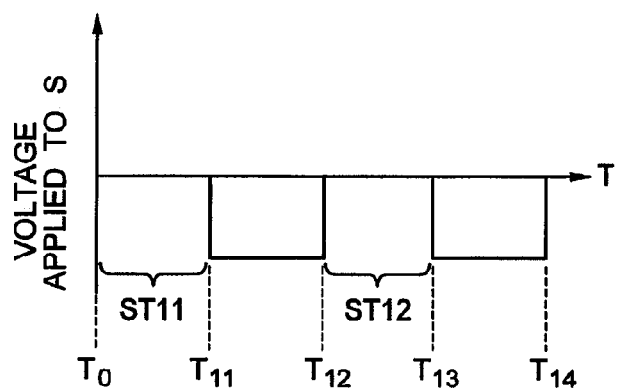
FIG. 23 is a timing chart showing an example of a control signal to a direct-current power supply.

More specifically, the control computer 22 generates a control signal and supplies the control signal to the direct-current power supply 12. The direct-current power supply 12 applies a direct-current voltage to the stage 19 to ease the electrification. As a result, a charge is supplied to the sample S. An example of such a control signal is shown in FIG. 23. In a timing chart shown in FIG. 23, the sample S is scanned with shots ST11 and ST12 of the electron beam EB during the time intervals T0 to T11 and T12 to T13. A pulse to apply a voltage to the stage 19 is generated during the time intervals T11 to T12 and T13 to T14 after the end of the shots ST11 and ST12.

Figure 24:
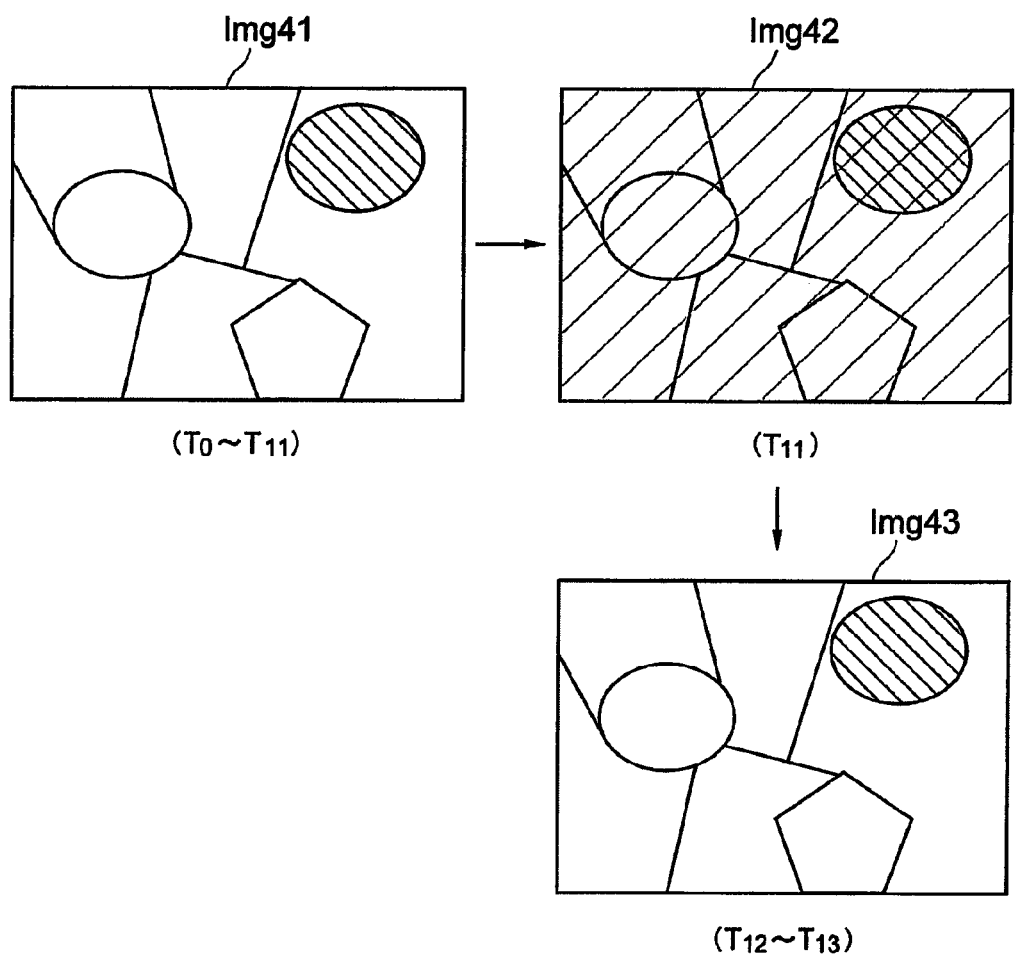
FIG. 24 is a diagram illustrating an example of how the electrification of a sample is eased according to Embodiment 6.

FIG. 24 is a diagram illustrating an example of how the electrification of the sample S is eased according to the present embodiment. An image indicated by a mark Img41 is an example of a two-dimensional contrast image obtained by the shot ST11 (see FIG. 23). A two-dimensional contrast image Img42 is obtained by simulation of a two-dimensional contrast image which would be obtained at a stage immediately after the shot ST11 without any electrification compensation. The overall luminance of the two-dimensional contrast image Img42 is lower than that of the two-dimensional contrast image Img41.

A two-dimensional contrast image Img43 is an example of a two-dimensional contrast image obtained by the shot ST12 (see FIG. 23). It is obvious that the luminance similar to that of the original two-dimensional contrast image Img41 is restored as a result of the electrification compensation by the direct-current power supply 12.

Figure 25:
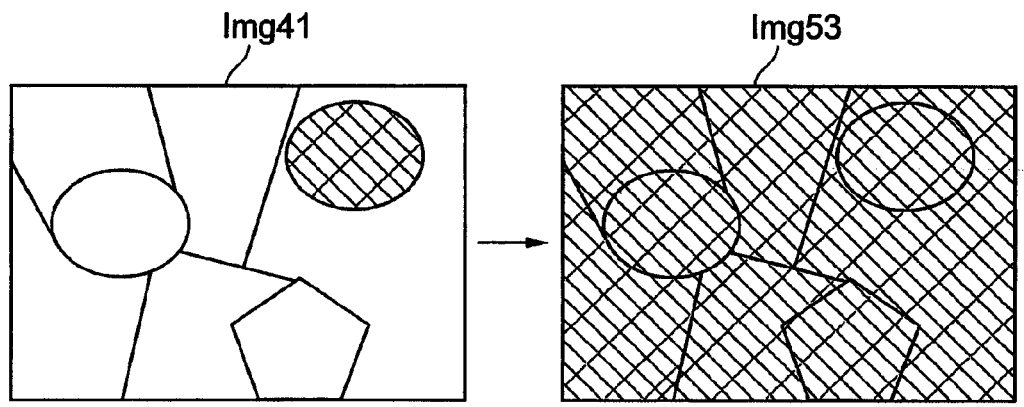
FIG. 25 is a diagram showing a specific example of two-dimensional contrast images according to a comparative example.

Conventionally, the next shot ST12 is applied after the electrification by the shot ST11 of the electron beam EB, so that as shown in a two-dimensional contrast image Img53 in FIG. 25, the overall luminance gradually decreases, and the analysis of the sample S is difficult.

According to the present embodiment, electrification compensation is made by applying a voltage to the sample S in accordance with the individual shot of the electron beam EB. Therefore, an image having satisfactory contrast is obtained for the sample S, and a highly precise sample analysis can be conducted.

Although a predetermined voltage is applied to the sample S in accordance with the individual shot of the electron beam EB in the example described above, the present inventions are not limited thereto. For example, the direct-current power supply 12 may be changed to a variable power supply, and a sample bias voltage may be controlled by the control computer 22 so that the current amount or voltage of the sample S will be constant. This allows a more precise sample analysis.

(7) Embodiment 7

In the observation of the sample S using the electron beam EB, some substances are sublimed by the application of the electron beam EB and vanish from the surface of the sample S. The present embodiment permits the identification of such a substance.

Figure 27:
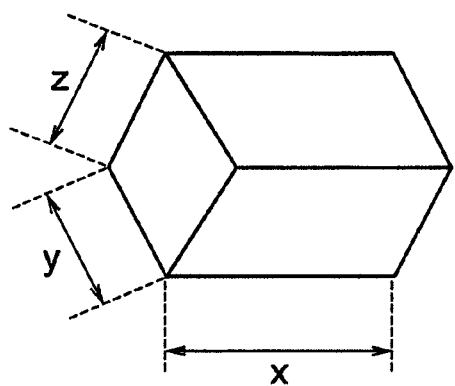
FIG. 27 is a diagram showing an example of an orthorhombic substance.

For example, in order to analyze an orthorhombic substance shown in FIG. 27, a two-dimensional contrast image of the sample S is acquired. The lengths (x, y, z) of three sides of the rectangular-parallelepiped crystal are measured from the obtained two-dimensional contrast image, and the volume of the crystal can thereby be found. Therefore, if the two-dimensional contrast image is properly acquired and measured during observation, the volume of the crystal can be continuously measured.

As the acceleration energy of the electron beam EB entering the sample S during observation and the amount of the electron beam per unit area and per unit time are controlled by the control computer 22, the amount of energy injected into the crystal per unit time is known. Therefore, if the vanishing speed of the crystal is known, the properties of the crystal can be identified. When there are a plurality of crystals on the surface of the sample S, the energy with which the crystals vanish in a vacuum device due to irradiation of charged particles can be more accurately estimated by performing measurements with varying energy of the electron beam EB.

Figure 26:
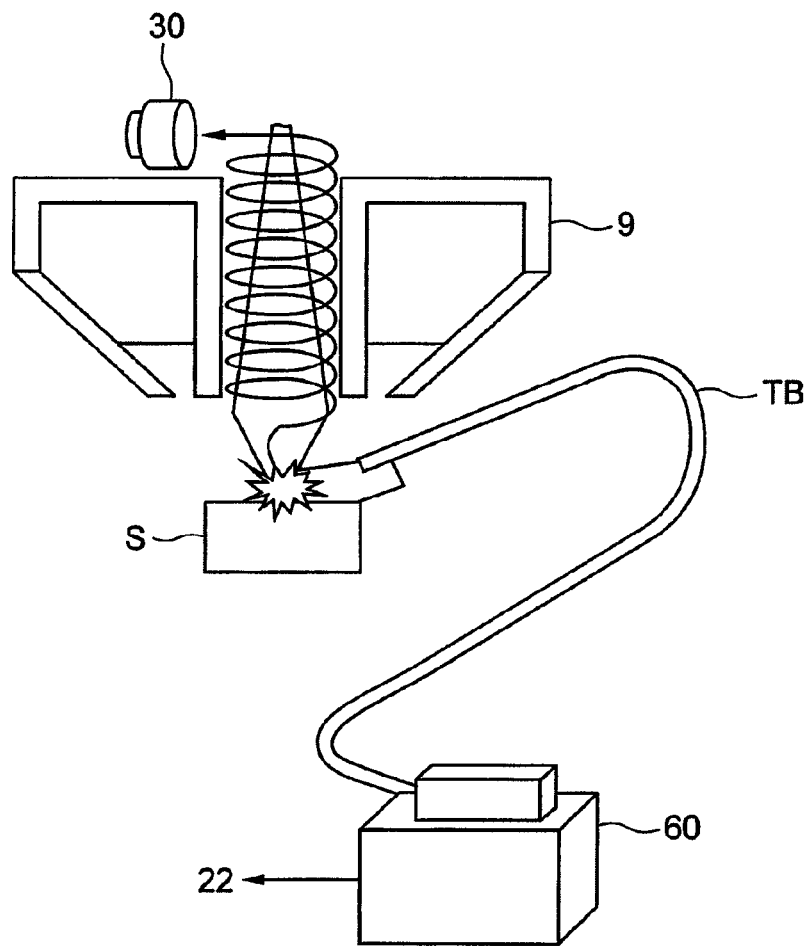
FIG. 26 is a diagram showing essential components of a sample analyzing apparatus according to Embodiment 7.

FIG. 26 is a diagram showing essential components of a sample analyzing apparatus according to Embodiment 7. The sample analyzing apparatus according to the present embodiment further includes a vanished substance measuring unit 60 in addition to the configuration in FIG. 1. The vanished substance measuring unit 60 has a tube TB having one end extending in the vicinity of the part of the sample S to which the electron beam EB is applied. Substances vanished from the sample S during the observation of the sample S are sucked in from the opening of the tube TB, and the amount of the vanished substances is measured by detecting the vapor. The tube TB is made of a non-electrified material such as an insulator.

The vanished substance measuring unit 60 is connected to the control computer 22, and sends the measurement result to the control computer 22. The control computer 22 finds the vanishing speed of the vanished substances from optical conditions of the electron beam EB attributed to the electron gun 1, for example, from the current amount of the electron beam EB and a scan time. The control computer 22 then calculates an energy amount necessary for sublimation and a sublimation point, and thereby identifies the vanished substances. The temperature of the sample S being analyzed can be estimated by measuring the temperature of the stage 19 with the stage temperature gauge 62. The pressure inside the column CL is monitored by the control computer 22 from the measurement result by the pressure gauge 64. Thus, the temperature and pressure at which the energy amount necessary for the sublimation is measured can be acquired at the same time.

A highly precise sample analysis can be conducted by the sample analyzing apparatus according to at least one of the embodiments described above.

Moreover, a highly precise sample analysis can be conducted by the sample analyzing method according to at least one of the embodiments described above.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A sample analyzing apparatus, comprising:
   a charged beam generating unit configured to generate a charged beam and apply the charged beam to a sample;
   a detecting unit configured to detect charged particles and then output a signal, the charged particles being generated from the sample by the application of the charged beam in a manner depending on a three-dimensional structure and material characteristics of the sample;

an analyzing unit configured to process the signal to analyze the sample;
a separating unit configured to separate the signal on the basis of the fact that the timing of the emission of the charged particles from the sample varies by the level of energy attributed to the presence of an elastic interaction within the sample; and
an image processing unit configured to process the signal and then generate a potential contrast image of the surface of the sample for each of the separated parts of the signal,
wherein the analyzing unit processes the generated potential contrast images to analyze the properties of the sample.

2. The apparatus of claim 1, wherein
the properties of the sample comprise the size of a crystal grain of a substance in the surface of the sample.

3. The apparatus of claim 1, further comprising:
a charged beam converging unit configured to converge the charged beam at different convergence angles in accordance with the material of the sample; and
an image processing unit configured to process the signal and then generate potential contrast images of the surface of the sample,
wherein the analyzing unit performs computing processing for the potential contrast images obtained at the different convergence angles, and thereby analyzes a material distribution in the surface layer of the sample.

4. The apparatus of claim 1,
wherein the detecting unit comprises a plurality of detectors corresponding to the level of the energy of the charged particles,
the apparatus further comprises a trajectory control unit which is provided between the sample and the detectors and which controls the trajectory of the charged particles by an electric field or a magnetic field in such a manner that the charged particles conforming to each energy classification enter the corresponding detector.

5. The apparatus of claim 4,
wherein the detectors comprise concentric rotationally symmetric detectors which are stacked apart from one another along the optical axis of the charged beam and which decrease in diameter with the increase in the distance from the sample.

6. The apparatus of claim 1,
wherein the detecting unit comprises a ring-shaped detector which is divided into regions in accordance with the crystal symmetry of the sample, and
the analyzing unit processes the signal for each of the regions, and thereby analyzes the crystal orientation of the sample to evaluate the crystallinity of the sample.

7. The apparatus of claim 6,
wherein the number of the regions is three or four, or a common multiple of three and four.

8. The apparatus of claim 1, further comprising:
a sample inclination angle control unit configured to incline the sample,
wherein the analyzing unit calculates the size of a crystal grain of the sample from the change of the signal with the change of the inclination angle of the sample.

9. The apparatus of claim 1, further comprising:
a scan unit configured to scan with the charged beam; and
an electrification compensating unit configured to apply a voltage to the sample to compensate for electrification resulting from the scanning with the charged beam.

10. The apparatus of claim 1, further comprising:
a vanished substance measuring unit configured to measure the amount of a substance vanished from the sample during the observation of the sample,
wherein the analyzing unit identifies the substance in accordance with the measurement result and optical conditions of the charged beam.

11. A sample analyzing method, comprising:
generating a charged beam and applying the charged beam to a sample;
detecting charged particles and then outputting a signal, the charged particles being generated from the sample by the application of the charged beam in a manner depending on a three-dimensional structure and material characteristics of the sample;
processing the signal to analyze the sample;
separating the signal on the basis of the fact that the timing of the emission of the charged particles from the sample varies by the level of energy attributed to the presence of an elastic interaction within the sample; and
processing the signal and then generating a potential contrast image of the surface of the sample for each of the separated parts of the signal,
wherein the analysis comprises processing the generated potential contrast images to analyze the properties of the sample.

12. The method of claim 11, further comprising:
converging the charged beam at different convergence angles in accordance with the material of the sample; and
processing the signal and then generating potential contrast images of the surface of the sample,
wherein the analysis comprises performing computing processing for the potential contrast images obtained at the different convergence angles, and thereby analyzing a material distribution in the surface layer of the sample.

13. The method of claim 11, wherein
the charged particles are detected in accordance with the crystal symmetry of the sample, and
the analysis further comprises analyzing the crystal orientation of the sample to evaluate the crystallinity of the sample.

14. The method of claim 11, further comprising:
scanning with the charged beam; and
applying a voltage to the sample to compensate for electrification resulting from the scanning with the charged beam.

15. The method of claim 11, further comprising:
measuring the amount of a substance vanished from the sample during the observation of the sample; and
identifying the substance in accordance with the measurement result and optical conditions of the charged beam.

* * * * *